US005770409A

United States Patent [19]

Pfefferle et al.

[11] Patent Number: 5,770,409

[45] Date of Patent: Jun. 23, 1998

[54] **FERMENTATIVE PREPARATION OF LYSINE WITH A STRAIN OF *C. GLUTAMICUM***

[75] Inventors: Walter Pfefferle, Halle; Hermann Lotter, Hainburg; Heinz Friedrich, Hanau; Wolfgang Degener, Bielefeld, all of Germany

[73] Assignee: Degussa Aktiengsellschaft, Frankfurt am Main, Germany

[21] Appl. No.: 677,911

[22] Filed: Jul. 10, 1996

Related U.S. Application Data

[63] Continuation of Ser. No. 198,374, Feb. 18, 1994, abandoned, which is a continuation of Ser. No. 942,804, Sep. 10, 1992, abandoned.

[30] Foreign Application Priority Data

Sep. 17, 1991 [DE] Germany .......................... 41 30 867.0

[51] Int. Cl.[6] .............................. C12P 13/08; C12P 13/04

[52] U.S. Cl. ........................ 435/115; 435/106; 435/252.1

[58] Field of Search .................................... 435/106, 115, 435/252.1

[56] References Cited

U.S. PATENT DOCUMENTS 4,411,997 10/1983 Shimazaki ............................... 435/115

FOREIGN PATENT DOCUMENTS

| | | | |
|---|---|---|---|
| 2488273 | 2/1982 | France . | |
| 0269167 | 6/1989 | Germany | 435/115 |
| 269167 | 6/1989 | Germany . | |

OTHER PUBLICATIONS

Inbar, "Natural–Abundance $^{13}C$ Nuclear Magnetic . . . *Brevibacterium flaium", Eur. J. Biochem.*, vol. 149, 601–607. 1985.

*Primary Examiner*—Irene Marx

*Attorney, Agent, or Firm*—Beveridge, DeGrandi, Weilacher & Young, LLP

[57] ABSTRACT

A process is disclosed for the fermentative preparation of amino acids, in which a strain of the genus Brevibacterium or Corynebacterium producing one or more amino acids is cultivated in a nutrient medium and the amino acids are isolated from the culture fluid at the end of fermentation. After the vigorous growth phase, the bacterial culture has at its disposal a smaller quantity of assimilable carbon source than it could metabolize on the basis of the structure of the strain and the quantity of other necessary supplements provided in the nutrient medium.

6 Claims, No Drawings

FERMENTATIVE PREPARATION OF LYSINE WITH A STRAIN OF *C. GLUTAMICUM*

This application is a continuation of application Ser. No. 08/198,374, filed Feb. 18, 1994, which is a continuation of 07/942,804, filed Sep. 10, 1992, which applications are entirely incorporated herein by reference and all abandoned.

BACKGROUND AND INTRODUCTION

The present invention relates to a process for the fermentative preparation of amino acids such as L-lysine or L-threonine.

L-Lysine is an essential amino acid and is used in large quantities as animal feed supplement. Numerous amino acids are generally produced biosynthetically which has long been known in the art. The bacterial strains for producing amino acids are distinguished by their capacity for secreting these amino acids into the culture medium at high concentrations within a short time. Feed batch processes are generally carried out to avoid high initial concentrations of substrate. Due to the very high metabolic capacity of the production strains used, it is of decisive importance to carry out the fermentation process in such a manner that the maximum values of oxygen requirement and of evolution of heat will be of an economically acceptable order of magnitude. Various strategies have therefore been employed to regulate the metabolic activity of the organisms so as to ensure the supply of oxygen and removal of heat and at the same time balance the distribution of formation of biomass and of product.

A process entailing intermittent feeding is disclosed in CSFR-PS 212 558 in which the metabolic activity during the growth phase is adjusted by changes in pH and the total amount of biomass is adjusted by the α-aminonitrogen. Soviet Patent 157 059 describes a process entailing intermittent feeding, in which the threonine concentration serves as the criterion for the feeding and the proportion of the reducing compound is maintained at 3 to 5%. A very finely adjusted process is disclosed in French Patent 8303487. In this process, two feed solutions are continuously added: A leucine phosphate solution which is added at such a rate that both the intensity of metabolism and the formation of the biomass are limited by the rate of addition of supplement. The second feed solution, a sugar solution, is supplied at such a rate that the actual sugar concentration is maintained at 5 to 15 g/l. This process shows that due to a limitation by the leucine/phosphate supplements during the feed phase, the culture uses less sugar at any point in time than is available in the culture medium. This procedure is in line with the repeatedly documented view that both C-limitation and undue C-excess should be avoided (e.g. East German Patent 269 167). Hadj Sassi et al. in "Biotechn. Letters, Volume 10, No. 8, pages 583–586 (1988)" even propose from 90 to 140 g/l of glucose for this purpose. The metabolic activity is therefore always regulated by a factor other than that of the source of C.

SUMMARY OF THE INVENTION

It is an object of the present invention to provide a process for the fermentative preparation of amino acids which proceeds at a higher degree of conversion of the source of carbon used (sugar) and in which a higher concentration of amino acids is obtained in the dry mass free from biomass.

This and other objects are achieved by a process for the fermentative preparation of amino acids in which a strain of the bacterial genus Brevibacterium or Corynebacterium producing one or more amino acids is cultivated in a nutrient medium and the amino acids produced are isolated from the culture fluid at the end of fermentation. It is a feature of the present invention that after the vigorous growth phase (during the production phase) a smaller quantity of utilizable source of carbon is available to the bacterial culture than it could usually metabolize based on the structure of the strain and the quantity of other necessary supplements provided in the nutrient medium. The fermentation (nutrient) medium is in other respects of conventional composition.

DETAILED DESCRIPTION OF THE INVENTION

In addition to containing sources of carbon such as assimilable sugars, sucrose, glucose, molasses or starch hydrolysates and ammonium ions, in the case of auxotrophic producers the medium contains complex components as a source of organic supplements (required due to one or more auxotrophies), such as protein hydrolysates as source of α-aminonitrogen, vitamins and inorganic salts. The vigorous growth at the beginning of fermentation is generally a logarithmic growth phase. This may be shortened if required by limiting the supplements and/or the source of carbon till the desired optical density is reached.

The logarithmic growth phase is followed by cell growth but the extent of this growth is confined to a small fraction of the vigorous growth phase. Strains producing L-lysine and/or L-threonine are preferably used. The fermentation medium is chosen so that the pH is from 6 to 8, preferably from 7 to 7.5, and the ammonium concentration is from 0.5 to 8 g/l; and the temperature is from 25° to 40° C., preferably from 30° to 36° C. The broth is stirred and as usually amply supplied with oxygen. Metabolization of the sugar may be controlled by the quantity of amino acid added, especially in the case of amino acid-auxotrophic lysine secretors. The concentration of these amino acid supplements or of other necessary supplements after the growth phase is advantageously from 0 to 0.1 g/l each, in particular from 0 to 0.05 g/l each. Thus, for example, in a leucine-auxotrophic lysine secretor, the sugar/leucine ratio in a continuously added feed medium is chosen so that the formation of biomass is limited by the supply of leucine but at the same time the amount of sugar provided is only a fraction of that which could be converted at the given leucine concentration.

The concentration of utilizable sugars after the vigorous growth phase is advantageously from 0 to <3 g/l, in particular from 0 to 1 g/l. The concentration of 0 g/l in the fermentation broth does not mean, either with respect to any supplements required or with respect to the source of carbon, that these substances are not supplied continuously. It means that these compounds are supplied in a quantity which is immediately taken up by the bacterial cultures.

This fermentation carried out by the process according to the invention has numerous very important advantages compared with the conventional processes mentioned above, namely:

1. The metabolic activity and hence the oxygen requirement and the evolution of heat of the culture can be influenced directly and without delay by the rate of supply of feed and adapted to the capacity of the fermenter.
2. The fermentation broths are distinguished by a higher product content of the dry mass as a whole and hence greater purity. Loss by the formation of by-products is prevented by the fact that over the whole period of feeding, the bacterial culture is offered less substrate than it would be capable of converting, so that the source of carbon constitutes the primary limitation (contrary to the prior art).

3. The fermentations have a higher yield than fermentations in which limitation is primarily by way of supplements.
4. In the process of monitoring the product, fermentation can be stopped directly and without any time lag at an optimum or at a plateau and the gross yield is at all times equal to the net yield.
5. In a working up project which includes direct concentration of the fermentation broth by evaporation, the fermenter contents can be immediately used for working up in the event of technical breakdown without the quality of the product being impaired by a high residual sugar content.

No special process to select appropriate strains is needed. The claimed fermentative preparation is suitable for all amino acid secreting strains of the *genera Brevibacterium* or Corynebacterium.

The Examples which follow illustrate specific embodiments of the process according to the invention, and show that optional strains excrete higher amounts of amino acids in comparison with the state of art.

EXAMPLES

Example 1 (Comparison Example)

5.1 kg of a sterile solution containing the following components were introduced into a fermentation container equipped with stirrer and ventilation system:

| | |
|---|---|
| Water | 4540 g |
| Molasses | 26 g |
| Glucose | 125 g |
| Corn gluten hydrolysate (hydrolysed with sulfuric acid) | 35 g |
| hydrolysate of the producer biomass (hydrolysed with sulfuric acid) | 320 g |
| Ammonium sulphate | 45 g |
| Phosphoric acid 85% | 7 g |
| Magnesium sulphate | 3 g |
| other mineral salts, traces and biotin and thiamine | |

and the solution was adjusted to pH 7.3 with ammonia solution. 0.6 1 of an inoculum of a *Corynebacterium glutamicum* DM 346-1 carrying the genetic markers leu, oxalysine resistance and aminoethyl resistance, were added to this solution at 33° to 35° C. The inoculum had been prepared by 15 hours' incubation at 33° C. and pH 7 with stirring and ventilation in a medium containing 4.4 mass percent of molasses in addition to 2% of sucrose and 14% of soya bean meal hydrolysate (hydrolysed with sulfuric acid) with the addition of 3% of ammonium sulphate, 0.05% of phosphoric acid and 0.02% of magnesium sulphate and the vitamins, biotin and thiamine.

With vigorous stirring, ventilation and adjustment of the pH to about 7.3 by means of aqueous ammonia solution, the following medium neutralized with aqueous ammonia solution was continuously added in the conventional manner within 32 hours after termination of the logarithmic growth phase in the main fermenter so that the measurable sugar concentration in the fermentation broth was from 5 to 35 g/l (enzymatic determination based on sucrose and glucose):

| | |
|---|---|
| Water | 1250 g |
| Molasses | 94 g |
| Glucose | 1465 g |
| Corn gluten hydrolysate (sulfuric acid) | 39 g |
| Hydrolysate of the producer biomass (sulfuric acid) | 265 g |
| Ammonium sulphate | 31 g |
| Phosphoric acid 85% | 4 g |
| Magnesium sulphate | 2 g |
| other mineral salts, traces and biotin and thiamine | |

At the end point of fermentation, when all the assimilable sugar in the fermentation medium has been used up, the degree of conversion of sugar into lysine was 35%, calculated as LysxHCl, and the lysine base content of the concentrated fermentation solution free from biomass was 45%.

Example 2

Preparation of the inoculum, the medium introduced into the main fermenter and the culture conditions are similar to those of Example 1.

Medium 2 also has the same composition with the exception of the following modification:

| | |
|---|---|
| Water | 1560 g |
| Molasses | 75 g |
| Glucose | 1170 g. |

In this experiment, the feed medium was added at the same rate as in Example 1. Analyses of the process based on assimilable sugar showed that, in accordance with the present invention, the measurable concentration of assimilable sugars remained lower than 3 g/l during the entire feed time and was almost always kept below 1 g/l. Analyses based on leucine in the fermentation broth, using amino acid analyzer, showed that after the quantity of leucine provided in medium 1 had been used up, the leucine concentration during the feed time was at no point greater than 0.05 g/l.

Unexpectedly, after termination of the fermentation, the degree of conversion of sugar into lysine (calculated as LysxHCl) was 40% and the lysine base content of the concentrated fermentation broth free from biomass was 54%.

Example 3

3980 kg of a sterile medium having the following composition were introduced into a 10 $m^3$ reactor:

| | |
|---|---|
| Sucrose | 320 kg |
| Molasses | 20 kg |
| Corn gluten hydrolysate | 230 kg |
| 25% Aqueous ammonium sulphate | 150 kg |
| Citric acid.$H_2O$ | 2.3 kg |
| Phospheric acid (89%) | 6.6 kg |
| $MgSO_4.7H_2O$ | 2.8 kg |
| $CaCl_2.2H_2O$ | 75 kg |
| $FeSO_4.H_2O$ | 113 kg |
| $MnSO_4.H_2O$ | 113 kg |
| $ZnSO_4.7H_2O$ | 5.6 g |
| $CuSO_4.5H_2O$ | 0.6 g |
| Biotin | 1.1 g |
| Thiamine.HCl | 0.8 g |
| $NH_4OH$ (2–3%) | 1010 kg |
| Water | 2258 kg |
| pH: 7.0. | |

The contents of the reactor are stirred at 33° C. and vigorously ventilated. After the transfer of 250 of inoculum of the strain DM 282-2 carrying the genetic markers leucine auxotrophic and aminoethylcysteine resistant (after 16 hours' incubation in a medium containing 6% of molasses, 14% of soya bean meal hydrolysate, 1% of ammonium sulphate and 0.1% of phosphoric acid at pH 7 and 30° C.) into a 10 $m^3$ reactor, the pH is maintained at 7.0 by means of aqueous ammonia and the rate of ventilation is adjusted so that the dissolved oxygen content is always above 15% saturation.

After the culture had grown to an optical density (535 nm) of about 30, a production medium having the following composition was added at the rate of 30 l/h:

| | |
|---|---|
| Sucrose | 940 kg |
| Molasses | 50 kg |
| Corn gluten hydrolysate | 180 kg |
| 25% Aqueous ammonium sulphate | 80 kg |
| Citric acid.$H_2O$ | 1 kg |
| Phosphoric acid (89%) | 2.8 kg |
| $MgSO_4.7H_2O$ | 1.2 kg |
| $FeSO_4.H_2O$ | 48 kg |
| $MnSO_4.H_2O$ | 48 kg |
| $ZnSO_4.7H_2O$ | 2.4 g |
| $CuSO_4.5H_2O$ | 0.3 g |
| Biotin | 0.6 g |
| Thiamine.HCl | 0.4 g |
| $NH_4OH$ (2–3%) | 80 kg |
| Water | 740 kg |
| pH: 7.5. | |

The pH was maintained at 7.3 during the production phase. In accordance with the present invention, a concentration of assimilable sugar of 1 g/l was not exceeded during the feed phase after the sugar provided in the growth medium had been used up, and the measurable leucine concentration was below 0.05 g/l. Unexpectedly, at the end of fermentation, the degree of conversion of sugar into lysine (in the form of Lys.HCl) was 32.3% and the lysine base content of the concentrated fermentation broth free from biomass was 54.7%.

Example 4 (Comparison Example)

Preparation of the inoculum, the process parameters and the media in the growth phase and in the production phase correspond to the conditions indicated in Example 3 although feeding was in this case carried out at a rate of about 100 l/h. As a result, the measurable concentrations of assimilable sugar during the feeding period after the sugar provided in the growth medium had been used up were always distinctly above 5 g/l but the concentration of leucine remained below 0.05 g/l. The degree of conversion of sugar into lysine (calculated as Lys.HCl) was 30.9% at the end of fermentation and the lysine base content of the fermentation broth free from biomass was 43.5%.

Example 5 (Comparison Example)

The media for culture, growth and production are similar in composition to the media of Example 1 except that the glucose was replaced by 25 g/l of sucrose in the growth medium and by 564 g/l of saccharose in the production medium. The incubation parameters including preparation of the inoculum are also identical. 0.82 Kg (0.8 1) of sterile growth medium were introduced into a small fermenter equipped with stirrer and ventilating means. To this solution were added 0.1 1 of an inoculum of *Corynebacterium glutamicum* DSM 5715 (deposited with the Deutsche Sammlung von Mikroorganismen und Zellkulturen (DSM), Mascheroder Weg 1B, D-38124 Braunschweig, Germany, on Dec. 19, 1989 under accession number DSM 5715) at 33° to 35° C. When an optical density of about 30 (535 nm) had been reached, 533 g (430 ml) of production medium were continuously added within 24 h.

During the time of feeding, the measurable sugar content was always above 5 g/l in the fermentation medium and the leucine content after the quantity provided in the growth medium had been used up was always below 0.05 g/l.

At the end of fermentation, 74 g of lysine were detected in the medium as Lys.HCl, which in the case of a total input of sucrose of 275 g corresponds to a degree of conversion of 27%. The lysine content of the total dry biomass was 30.5%.

Example 6

In another experiment also using strain DSM 5715, in which all the parameters of media and incubation were identical to those of Example 5, the production medium was continuously fed in within 39 h. In accordance with the present invention, the actual sucrose concentration during the feed period after the source of C and leucine provided in the growth medium had been used up was below 1 g/l and the leucine concentration was below 0.05 g/l. Unexpectedly, at the end of fermentation, 89 g of lysine (in the form of lysine.HCl) were detected in the medium, and the degree of conversion was 32%. The lysine base content in the total dry mass was 36.3%.

Further variations and modifications of the invention will become apparent to those skilled in the art from the foregoing and are intended to be encompassed by the claims appended hereto.

German Priority Application P 41 30 867.0, filed on Sep. 17, 1992, is relied on and incorporated by reference.

What is claimed:

1. A process for the fermentative preparation of L-lysine, said process comprising;

(a) cultivating the bacterial strain *Corynebacterium glutamicum DSM* 5715, in a nutrient medium in order to produce L-lysine, (b) continuously feeding said strain with an amount of sugar sufficient to maintain the sugar concentration in the nutrient medium at a concentration of less than 3 g/l for a time sufficient to accumulate L-lysine in the nutrient medium, and (c) isolating said L-lysine;

wherein said sugar is sucrose or glucose.

2. The process according to claim 1, wherein a source of said sugar is molasses.

3. The process according to claim 1, wherein the concentration of said sugar is less than 1 g/l.

4. The process according to claim 3 wherein a source of said sugar is molasses.

5. A process for the fermentative preparation of L-lysine, said process comprising;

(a) cultivating the bacterial strain *Corynebacterium glutamicum* DSM 5715 in a nutrient medium containing sugar in order to produce L-lysine, (b) maintaining the sugar concentration of the nutrient medium below 3 g/l, (c) isolating said L-lysine;

wherein said sugar is sucrose or glucose.

6. The process according to claim 5 wherein a source of said sugar is molasses.

* * * * *